US009726615B2

(12) United States Patent
Huang et al.

(10) Patent No.: US 9,726,615 B2
(45) Date of Patent: Aug. 8, 2017

(54) SYSTEM AND METHOD FOR SIMULTANEOUS DARK FIELD AND PHASE CONTRAST INSPECTION

(71) Applicant: KLA-Tencor Corporation, Milpitas, CA (US)

(72) Inventors: Chuanyong Huang, San Jose, CA (US); Qing Li, San Jose, CA (US); Donald Pettibone, San Jose, CA (US); Buzz Graves, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/804,296

(22) Filed: Jul. 20, 2015

(65) Prior Publication Data
US 2016/0025645 A1 Jan. 28, 2016

Related U.S. Application Data

(60) Provisional application No. 62/027,393, filed on Jul. 22, 2014.

(51) Int. Cl.
*G01N 21/00* (2006.01)
*G01N 21/88* (2006.01)
*G01N 21/95* (2006.01)

(52) U.S. Cl.
CPC ..... *G01N 21/8806* (2013.01); *G01N 21/9501* (2013.01); *G01N 2021/8825* (2013.01)

(58) Field of Classification Search
CPC ............... G01N 21/9501; G01N 32/94; G01N 21/8806; G01N 21/956; G01N 21/95607
(Continued)

(56) References Cited

U.S. PATENT DOCUMENTS

| 5,798,829 A | 8/1998 | Vaez-Iravani |
| 7,345,754 B1 | 3/2008 | Zhao et al. |

(Continued)

FOREIGN PATENT DOCUMENTS

WO 2013134068 A1 9/2013

OTHER PUBLICATIONS

PCT Search Report for PCT/US2015/041409, dated Oct. 28, 2015, 3 pages.

*Primary Examiner* — Tarifur Chowdhury
*Assistant Examiner* — Md M Rahman
(74) *Attorney, Agent, or Firm* — Suiter Swantz pc llo (57) ABSTRACT

An inspection apparatus for simultaneous dark field (DF) and differential interference contrast (DIC) inspection includes an illumination source and a sample stage configured to secure a sample. The inspection apparatus includes a first sensor, a second sensor and an optical sub-system. The optical sub-system includes an objective, one or more optical elements arranged to direct, through the objective, illumination from the one or more illumination sources to a surface of the sample. The objective is configured to collect a signal from the surface of the sample, wherein the collected signal includes a scattering-based signal and/or a phase-based signal from the sample. The inspection apparatus includes one or more separation optical elements arranged to spatially separate the collected signal into a DF signal and a DIC signal by directing the DF signal and the DIC signal along a DF path and DIC path respectively.

24 Claims, 4 Drawing Sheets

(58) Field of Classification Search
USPC .................................................... 356/237.2
See application file for complete search history.

(56) References Cited

U.S. PATENT DOCUMENTS

| | | |
|---|---|---|
| 7,560,675 B2 | 7/2009 | Takahashi |
| 7,728,969 B2 | 6/2010 | Saito et al. |
| 8,355,140 B2 | 1/2013 | Hwang et al. |
| 8,384,903 B2 | 2/2013 | Nielsen et al. |
| 8,624,967 B2 | 1/2014 | O'Connell et al. |
| 2003/0215791 A1 | 11/2003 | Garini et al. |
| 2005/0254065 A1* | 11/2005 | Stokowski ....... G01N 21/95684 356/601 |
| 2008/0225275 A1 | 9/2008 | Nielsen et al. |
| 2009/0059215 A1 | 3/2009 | Mehanian et al. |
| 2009/0180176 A1* | 7/2009 | Armstrong ......... G02B 17/0812 359/366 |
| 2009/0279080 A1 | 11/2009 | Danner et al. |
| 2011/0181891 A1 | 7/2011 | Hwang et al. |
| 2012/0176475 A1 | 7/2012 | Xu et al. |
| 2013/0050689 A1 | 2/2013 | Reich et al. |
| 2013/0252237 A1 | 9/2013 | Wagner |
| 2014/0050389 A1 | 2/2014 | Mahadevan et al. |
| 2014/0169698 A1* | 6/2014 | Stampanoni ........... A61B 6/483 382/284 |
| 2014/0285650 A1* | 9/2014 | Ishiwata ............ G06K 9/00127 348/79 |

\* cited by examiner

SYSTEM AND METHOD FOR SIMULTANEOUS DARK FIELD AND PHASE CONTRAST INSPECTION

CROSS-REFERENCE TO RELATED APPLICATION

The present application claims the benefit under 35 U.S.C. §119(e) of U.S. Provisional Application Ser. No. 62/027,393, filed Jul. 22, 2014, entitled APPARATUS AND METHODOLOGY FOR SIMULTANEOUS DARK FIELD AND PHASE CONTRAST INSPECTION, naming Chuanyong Huang, Qing Li, Donald Pettibone and Buzz Graves as inventors, which is incorporated herein by reference in the entirety.

TECHNICAL FIELD

The present invention generally relates to defect detection and classification, and, more particularly, to simultaneous dark field inspection and differential interference contrast inspection.

BACKGROUND

As tolerances on semiconductor device fabrication processes continue to narrow, the demand for improved semiconductor wafer inspection tools continues to increase. Types of inspection tools suitable for wafer inspection include a dark field (DF) inspection tool, which utilizes scattering information from a sample (e.g., semiconductor wafer), and a differential interference contrast inspection tool, which utilizes phase information from a sample. Typically, when seeking both DF and DIC information, a given inspection tool or microscope operates independently in either DF mode or DIC mode due to differences and/or incompatibilities in optical components, optical layout and the detection signal. Although it is possible to run different optical layouts separately to detect DF and DIC signals separately, it is time-consuming, and sometimes impossible, to combine two separated signals during the observation of a moving sample (e.g., biological living cell). In the semiconductor fabrication industry, it is important for inspection equipment to be capable of quickly locating and classifying one or more defects. As a result, performing DF and DIC inspection in separate operations reduces value to the wafer inspection process. Therefore, it would be advantageous to provide a system and method that cures the defects identified in the previous art.

SUMMARY

An apparatus for simultaneous dark field and differential interference contrast inspection is disclosed, in accordance with an illustrative embodiment of the present disclosure. In one illustrative embodiment, the apparatus includes one or more illumination sources. In another illustrative embodiment, the apparatus includes a sample stage configured to secure a sample. In another illustrative embodiment, the apparatus includes a first sensor and a second sensor. In another illustrative embodiment, the apparatus includes an optical sub-system comprising: an objective; and one or more optical elements arranged to direct, through the objective, illumination from the one or more illumination sources to a surface of the sample, wherein the objective is configured to collect a collected signal from the surface of the sample, wherein the collected signal includes at least one of a scattering-based signal and a phase-based signal from the sample; and one or more separation optical elements arranged to spatially separate the collected signal into a dark field signal and a differential interference contrast signal by directing the dark field signal along a dark field path to the first sensor and the differential interference contrast signal along a differential interference contrast path to the second sensor.

An apparatus for simultaneous dark field and differential interference contrast inspection is disclosed, in accordance with an additional illustrative embodiment of the present disclosure. In one illustrative embodiment, the apparatus includes one or more illumination sources, a sample stage configured to secure a sample, and an optical sub-system. In another illustrative embodiment, the optical sub-system includes an objective, a mirrored pupil mask configured to transmit illumination having an NA below a selected NA threshold, and one or more optical elements arranged to direct illumination having an NA below the selected NA threshold through the mirrored pupil mask. In another illustrative embodiment, the one or more optical elements are further configured to direct illumination transmitted through the mirrored pupil mask through the objective and to a surface of the sample. In another illustrative embodiment, the objective is configured to collect a signal from the surface of the sample. In another illustrative embodiment, the collected signal includes at least one of a scattering signal and a phase signal from the sample. In another illustrative embodiment, the mirrored pupil mask is further configured to spatially separate the collected signal into a dark field signal and a differential interference contrast signal by reflecting a portion of the collected illumination having an NA above the selected NA threshold along a dark field path to a first sensor and transmitting a portion of the collected illumination having an NA below the selected NA threshold along the differential interference contrast path to a second sensor.

An apparatus for simultaneous dark field and differential interference contrast inspection is disclosed, in accordance with an additional illustrative embodiment of the present disclosure. In one illustrative embodiment, the apparatus includes one or more illumination sources, a sample stage configured to secure a sample, and an optical sub-system. In another illustrative embodiment, the apparatus includes an objective, one or more optical elements configured to direct illumination through the objective and to a surface of the sample, wherein the objective is configured to collect a collected signal from the surface of the sample, wherein the collected signal includes at least one of a scattering signal and a phase signal from the sample, a beam splitter configured to direct a first portion of the collected illumination along a dark field path, wherein the beam splitter is further configured to transmit a second portion of the collected illumination along the differential interference contrast path, a pupil block disposed along the dark field path and configured to block illumination having an NA below a selected NA threshold, and a pupil mask disposed along the differential contrast interference path and configured to block illumination having an NA above the selected NA threshold. In another illustrative embodiment, the apparatus includes a first sensor configured to collect illumination transmitted by the pupil block of the dark field path. In another illustrative embodiment, the apparatus includes a second sensor configured to collect illumination transmitted by the pupil mask of the differential interference contrast path.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying FIGURES in which.

DETAILED DESCRIPTION OF THE INVENTION

Reference will now be made in detail to the subject matter disclosed, which is illustrated in the accompanying drawings.

Referring generally to FIGS. 1A through 1D, a system and method for simultaneous dark field (DF) and differential interference contrast (DIC) inspection is described in accordance with the present disclosure. U.S. Pat. No. 5,798,829 to Vaez-Iravani, issued on Aug. 25, 1998, discloses the separate measurement of DF and DIC signals from a sample using a single laser, which is incorporated herein by reference in its entirety. U.S. Pat. No. 7,345,754 to Zhao, issued on Mar. 18, 2008, discloses the use of a bright field (BF) inspection system for carrying out DF inspection, which is incorporated herein by reference in its entirety.

The simultaneous analysis of a scattering-based DF signal and a phase-based DIC signal may significantly enhance the detection and classification of defects (or other features) of a given sample. The DF signal and DIC signal are often sensitive to different sample and defect features, allowing for a fusion of the signals to enhance the overall understanding of the sample 103 (and associated defects or features).

Embodiments of the present disclosure are directed to the simultaneous operation of scattering-based dark field (DF) and phase-based differential interference contrast (DIC) modes in an inspection tool. Such a configuration provides for the simultaneous acquisition of scattering-based and phase-based information from the sample. Embodiments of the present disclosure serve to combine components of DF and DIC modes to detect and classify defects of a sample (e.g., point defects, stacking defects and the like). Some embodiments of the present disclosure are directed to an optical sub-system including one or more optical components suitable for illuminating the sample with illumination of a selected NA (e.g., pupil mask with low NA pass, pupil mask with high NA pass and the like) through a single objective. Additional embodiments of the present disclosure serve to collect both the scattering-based DF signal and the phase-based DIC signal from the sample with the single objective. In additional embodiments, the optical sub-system separates the DF signal from the DIC signal. For example, the optical sub-system may be configured so as to reflect a conjugate region of the collected illumination as the DF signal. For instance, high NA light (i.e., light having an NA above a selected NA threshold) may be reflected along a DF path in the case where low NA light (i.e., light having an NA below the selected NA threshold) was passed to the sample during illumination of the sample. In another instance, low NA light may be reflected along a DF path in the case where high NA light was passed to the sample during illumination of the sample. In addition, the balance of light (i.e., light not reflected as DF signal along the DF path) is passed as the DIC signal along a DIC path.

Embodiments of the present disclosure may carry out a data fusion procedure to detect and/or classify defects by fusing the simultaneously acquired DF and DIC data. Additional embodiments of the present disclosure may carry out sample characterization by analyzing DF and DIC data separately.

Figure 1A:
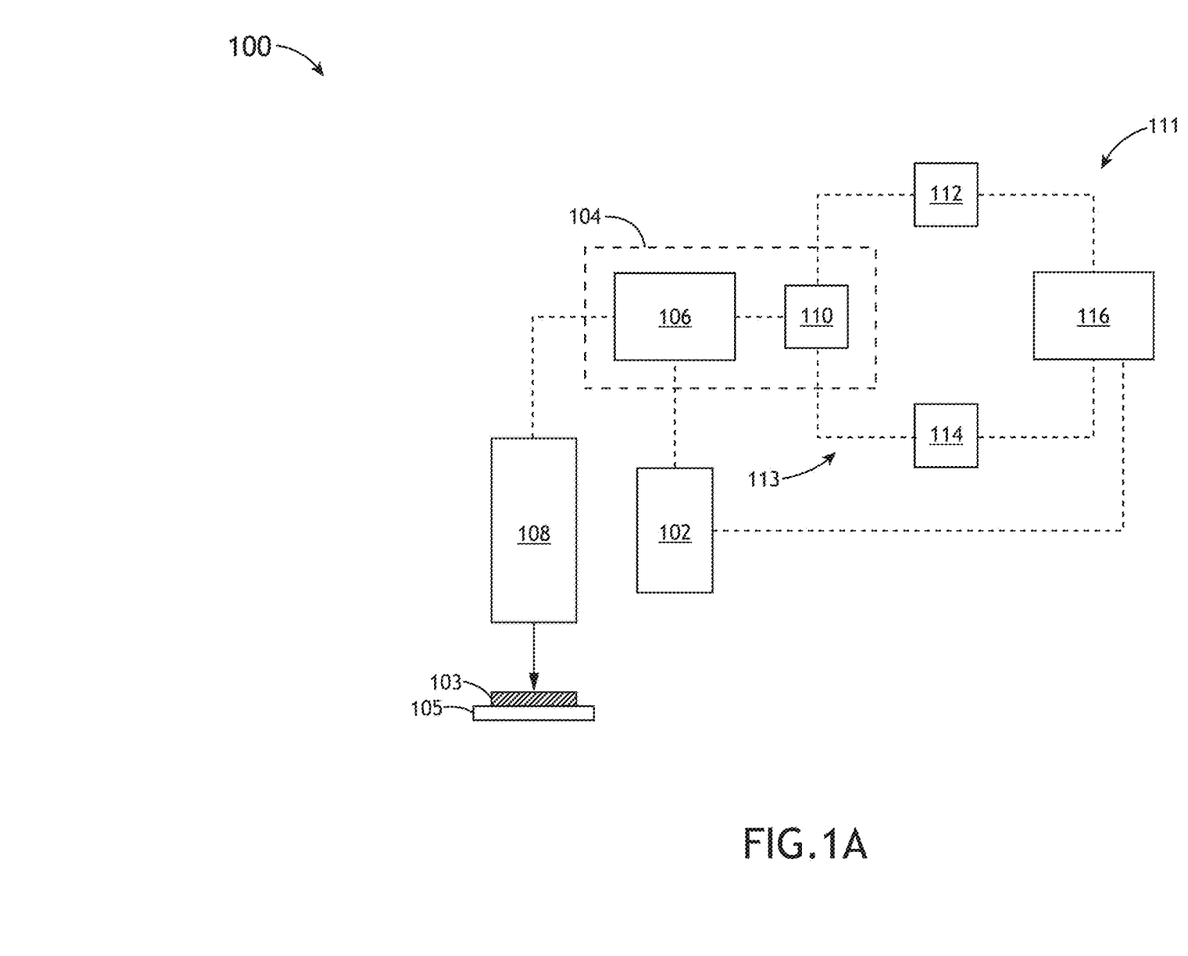
FIG. 1A is a conceptual view of system for simultaneous dark field and differential interference contrast inspection, in accordance with one embodiment of the present disclosure.

FIG. 1A illustrates a conceptual view of a system 100 for simultaneous DF and DIC inspection, in accordance with one embodiment of the present disclosure. In one embodiment, the system 100 includes an illumination source 102. The illumination source 102 may include any illumination source known in the art of DF and/or DIC based inspection. For example, the illumination source 102 may include, but is not limited to, a narrowband illumination source. For instance, the illumination source 102 may include, but is not limited to, a laser (e.g., diode laser). In one embodiment, the illumination source 102 includes, but is not limited to, a dithered diode laser.

In one embodiment, the system 100 includes a sample stage 105 for securing one or more samples 103 (e.g., one or more semiconductor wafers). The sample stage may include any sample stage known in the art of inspection. For example, the sample stage 105 may include, but is not limited to, a rotational sample stage, a linear sample stage or a combination of a rotational sample stage and a linear sample stage.

In one embodiment, the system 100 includes an optical sub-system 104. The optical sub-system 104 may include any number and type of optical components necessary for directing illumination from the illumination source 102 to the sample 103, collecting the scattering-based DF and phase-based DIC signals from sample 103, separating the DF and DIC signals and/or directing the DF and DIC signals along DF and DIC pathways 111,113 respectively.

In one embodiment, the optical sub-system 104 includes one or more optical elements 106 for directing illumination from the illumination source 102 to a surface of a sample 103 and/or conditioning the illumination from the illumination source 102. For example, the one or more optical elements 106 of optical sub-system 104 may include, but are not limited to, one or more beam splitters, one or more lenses, one or more pupil masks, one or more mirrors, one or more filters or one or more polarizers.

In another embodiment, the one or more optical elements 106 of the optical sub-system 104 are arranged to direct illumination from the illumination source 102 to the sample 103 through the objective 108. In another embodiment, the objective 108 is arranged so as to collect both the DF signal and the DIC signal from the sample 103. In this regard, light scattered from the sample 103 is collected by the objective 108 as the DF signal, while imaging light or small-shear reflected light is collected by the objective 108 as the DIC signal. The DIC signal includes phase information, whereby components of the DIC signal may interfere with each other at downstream optical components (e.g., Wollaston prism—see FIG. 1B; dark field filter and the like) and phase information is later extracted (e.g., extracted via 2-D sensor 114).

In an alternative embodiment, one or more optical elements 106 of the optical sub-system 104 may be arranged such that the sample 103 is illuminated along an illumination path outside of the objective. For example, the optical sub-system 104 may be arranged so as to provide oblique incident light on the sample 103.

In another embodiment, the optical sub-system 104 includes one or more separation optical elements 110 arranged to spatially separate the scattering-based DF signal from the phase-based DIC signal. In this regard, the one or more separation optical elements 110 may direct the DF signal along a DF path 111 to a first sensor 112, also referred to herein as the "DF sensor." Further, the one or more separation optical elements 110 may direct the DIC signal along a DIC path 113 to a second sensor 114, also referred to herein as the "DIC sensor."

The one or more separation optical elements 110 may include any number and type of optical components for separating the DF and DIC signal along different optical paths. In one embodiment, as discussed further herein in FIG. 1B, the one or more separation optical elements 110 may include a reflective pupil mask or "pupil pick-off mirror," which passes through or transmits (e.g., along the DIC path 113) illumination having an NA below a selected threshold and reflects illumination (e.g., along the DF path) having an NA above the selected threshold. It is further noted that the one or more separation elements 110 may be configured such that illumination reflected along the DF path 111 by the one or more separation elements 110 is conjugate to the illumination selected to pass through, based on NA, to sample 103. For example, the one or more separation elements 110 may pass through, or transmit, low NA illumination to the sample 103, while reflecting high NA illumination along the DF path 111 (and then passing low NA phase-based DIC signal along the DIC path 113). By way of another example, the one or more separation elements 110 may transmit high NA illumination to the sample 103, while reflecting low NA illumination along the DF path 111 (and then passing high NA phase-based DIC signal along the DIC path 113).

Figure 1B:
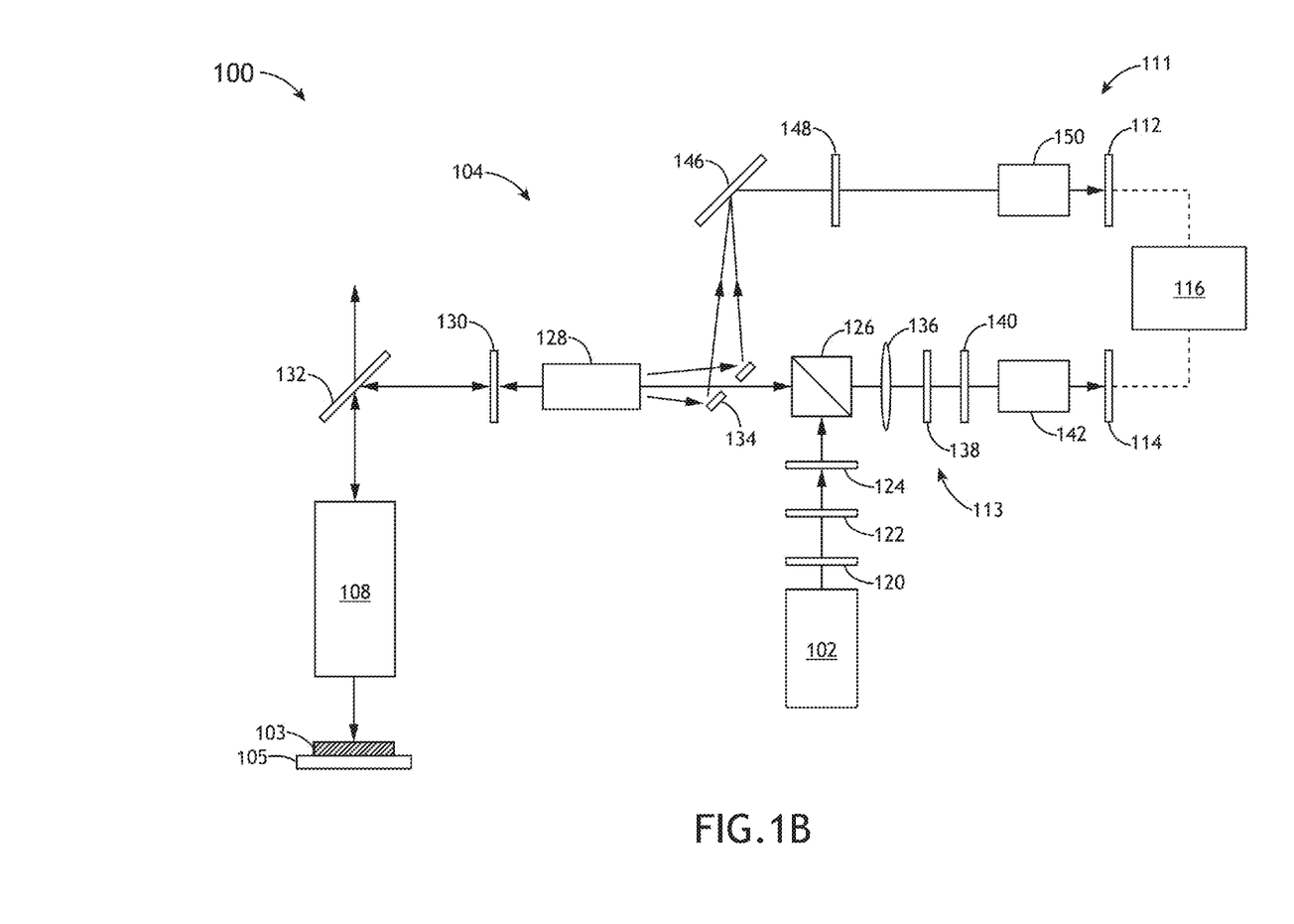
FIG. 1B is a simplified schematic view of system for simultaneous dark field and differential interference contrast inspection, in accordance with one embodiment of the present disclosure.
Figure 1C:
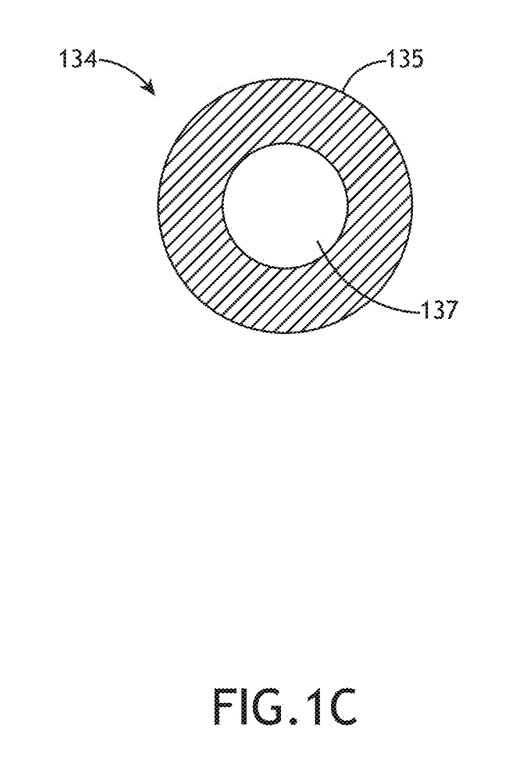
FIG. 1C is a simplified schematic view of a mirror pupil mask for use in the system for simultaneous dark field and differential interference contrast inspection, in accordance with one embodiment of the present disclosure.
Figure 1D:
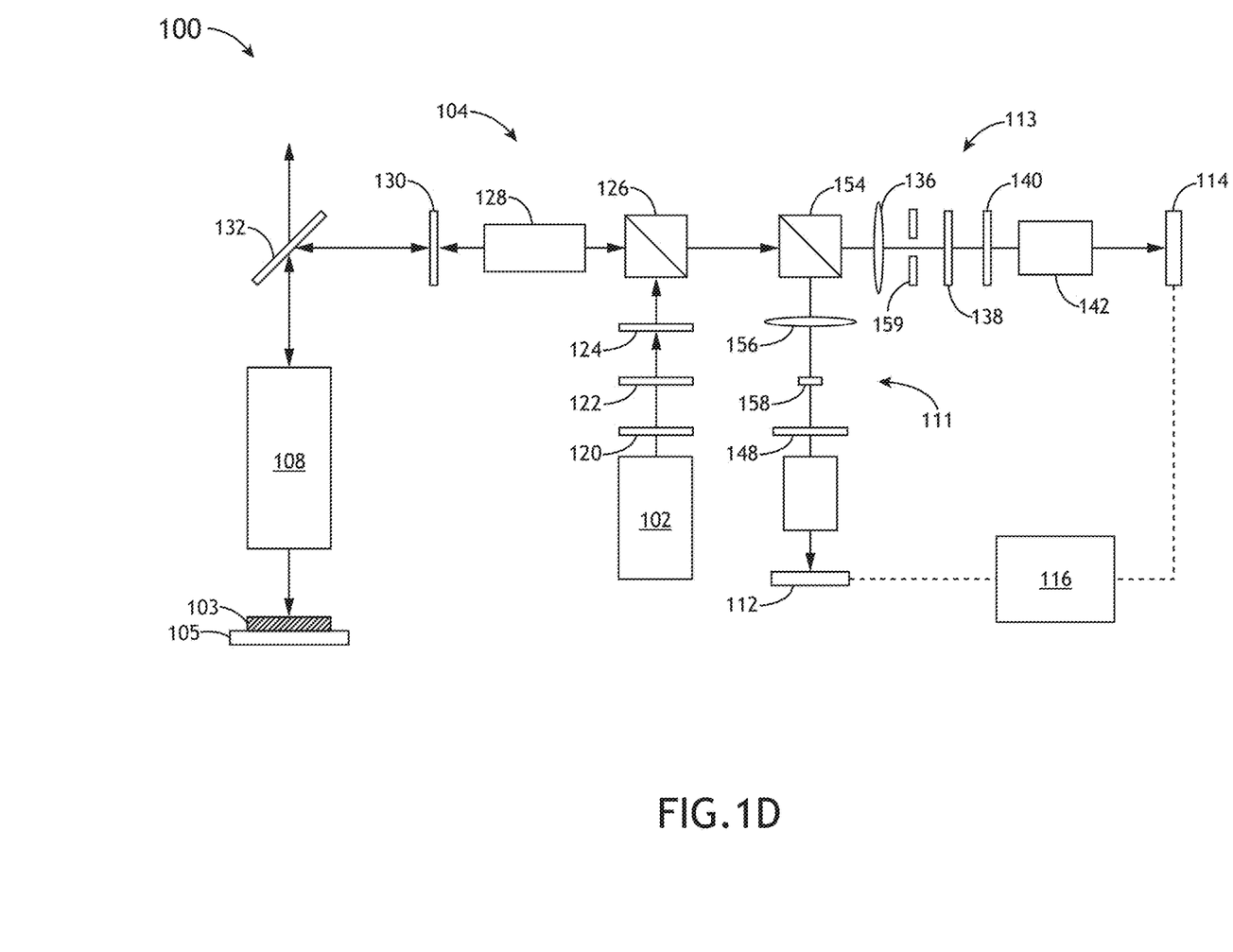
FIG. 1D is a simplified schematic view of system for simultaneous dark field and differential interference contrast inspection, in accordance with one embodiment of the present disclosure.

In another embodiment, as discussed further herein in FIG. 1D, the one or more separation optical elements 110 may include a beam splitter configured to direct the DF signal along the DF path 111, while transmitting the DIC signal along the DIC path 113. This embodiment is discussed in greater detail further herein.

It is noted that the first sensor 112 and/or the second sensor 114 may include any optical sensors known in the art of optical inspection. For example, the first sensor 112 and/or the second sensor 114 may include, but are not limited to, one or more CCD sensors, one or more TDI-CCD sensors, one or more PMT sensors, one or more cameras and the like. It is further noted that the DIC sensor 114 may include any two-dimensional sensor known in the art.

In one embodiment, the controller 116 includes one or more processors (not shown) and a non-transitory storage medium (i.e., memory medium). In this regard, the storage medium of the controller 116 (or any other storage medium) contains program instructions configured to cause the one or more processors of controller 116 to carry out any of the various steps described through the present disclosure. For the purposes of the present disclosure, the term "processor" may be broadly defined to encompass any processor or logic element(s) having processing capabilities, which execute instructions from a memory medium. In this sense, the one or more processors of controller 116 may include any microprocessor-type device configured to execute software algorithms and/or instructions. In one embodiment, the one or more processors may include a desktop computer or other computer system (e.g., networked computer) configured to execute a program configured to execute the computational/data processing steps described throughout the present disclosure. It should be recognized that the steps described throughout the present disclosure may be carried out by a single computer system, multiple computer systems, or a multi-core processor. Moreover, different subsystems of the system 100, such as a display device or a user interface device (not shown), may include a processor or logic elements suitable for carrying out at least a portion of the steps described above. Therefore, the above description should not be interpreted as a limitation on the present disclosure, but rather merely an illustration FIG. 1B illustrates a simplified schematic of system 100, in accordance with one embodiment of the present disclosure. The optical sub-system 104 depicted in FIG. 1B includes a mirrored pupil mask 134 arranged to separate the DF signal and DIC signal collected from the sample 103. In one embodiment, the mirrored pupil mask 134, or pick-off mirror, as depicted in FIG. 1C, includes a mirrored annulus 135 and aperture 137 configured to pass low NA illumination (i.e., illumination having an NA below a selected threshold) from the illumination source 102 through to the sample 103, while reflecting high NA illumination (i.e., illumination having an NA above a selected threshold) collected from the sample 103 along the DF path 111 and toward the DF sensor 112. In another embodiment, although not shown, the mirrored pupil mask 134, or pick-off mirror, serves to pass high NA illumination from the illumination source 102 through to the sample 103, while reflecting low NA illumination collected from the sample 103 along the DF path 111 and toward the DF sensor 112. In this regard, the illumination of the mirror pupil mask 134 is conjugate to the illumination passed through the aperture of the mirror pupil mask 134 and to the sample 103.

In addition to the pupil mask 134, the optical sub-system 104 of FIG. 1B may include any number and type of optical components for directing, conditioning, and/or selecting illumination from the illumination source 102 and/or scattered or reflected illumination collected from the sample 103.

The illumination of interest may be processed by various optical elements such as, but not limited to, one or more polarizers, one or more wave plates, one or more beam shape components, one or more filters, one or more folding mirrors prior to entering the objective 108 and illuminating the sample 103. For example, as shown in FIG. 1B, illumination from the illumination source 102 may be transmitted through the OD 120 (e.g., 3 position) and through a polarizer 122 and wave plate 124 (e.g., quarter wave plate). Then, a beam splitter 126 may direct some of the illumination from the illumination source 102 along an illumination path, with a portion of the illumination passing through mirrored pupil mask 134 (as described above). After a selected portion of the illumination passes through the mirrored pupil mask 134, the afocal lens 128 may transmit the selected illumination through filter 130 (e.g., 405 nm filter). Then, the turning mirror 132 may direct the filtered illumination through the objective 108 and to the sample 103 disposed on the sample stage 105. In one embodiment, the turning mirror 132 includes a dichroic mirror for reflecting a selected wavelength of light of the collected signal to downstream components for characterization, while transmitting an undesired wavelength or set of wavelengths collected from the sample along an additional path (e.g., additional path to a beam dump).

In another embodiment, the objective 108 collects the illumination scattered from the sample 103 for form the DF signal. The DF signal is then reflected by mirror 132 and directed back along the optical path through the filter 130 and afocal lens 128. Then, the collected illumination again impinges on the mirrored pupil mask 134, which serves to separate the collected signal from the sample into DF and DIC components. This is carried out by reflecting illumination of a selected NA regime (e.g., low NA or high NA) along the DF path 111 and transmitting the remaining illumination (e.g., high NA or low NA) to the DIC path 113. For example, in the case where low NA illumination was passed through to the sample 103, the mirrored phase mask 134 may reflect high NA illumination to the DF path 111 (and transmit low NA illumination to the DIC path 113). By way of another example, in the case where high NA illumination was passed through to the sample 103, the mirrored phase mask 134 may reflect low NA illumination to the DF path 111 (and transmit high NA illumination to the DIC path 113). The illumination directed along the DF path 111 via the mirrored pupil mask 134 may then be focused onto the DF sensor 112 (e.g., 1-D sensor suitable for large particle monitoring) via lens 142 (e.g., tube lens).

Simultaneous to the collection of the DF signal, imaging and/or small-shear reflected illumination containing phase information may be collected by objective 108 and passed through the aperture of the mirror pupil mask 134. Then, the component signals of the DIC signal interfere with each other at the prism 138 (e.g., Wollaston prism) or filter. In one embodiment, the system 100 includes one or more lenses 136 for focusing the DIC signal. In another embodiment, an analyzer 140 (e.g., switchable analyzer) may be used to suppress the noise contribution in the polarized signal. In turn, following suppression of the noise, the signal may be focused onto the DIC sensor 114 (e.g., 2-D sensor) suitable for extracting phase information from the DIC signal via lens 142 (e.g., tube lens).

In another embodiment, the controller 116 may acquire the measured DF signal from the DF sensor 112 and the measured DIC signal from the DIC sensor 114. In another embodiment, the controller 116 may perform a data fusion process, whereby the measured DF signal from the DF sensor 112 is fused, or combined, with the measured DIC signal from the DIC sensor 114. In this regard, the controller 116 may combine and/or compare one or more portions of the DF signal with/to one or more portions of the DIC signal to characterize one or more features (e.g., defects) of the sample 103. In another embodiment, the controller 116 may display imagery data associated with the DF signal and the DIC signal to a user via a user interface (not shown). In this regard, the user (or algorithm executed by the controller 116) may then analyze the DF signal, which includes scattering information, and the DIC signal, which includes phase information, simultaneously.

It is again noted that the simultaneous analysis of the scattering-based DF signal and the phase-based DIC signal may significantly enhance the detection and classification of defects (or other features) of the sample 103. The DF signal and DIC signal are often sensitive to different sample and defect features, allowing for a fusion of the signals to enhance the overall understanding of the sample 103 (and associated defects or features). For instance, in the case of stacking defects, a DF-based inspection process often mischaracterizes a stacking defect as a point defect or fails to detect the defect altogether. In contrast, the DIC signal measured by the DIC sensor 114 provides for the detection of defects that are no taller than a few wavelengths of the utilized illumination. In the case where the illumination source 102 provides illumination in the 200-500 nm range (e.g., 405 nm), the DIC sensor 114 is likely to be sensitive to features that are as short as 0.5 µm. In this sense, DIC-based inspection is superior to topographical studies and provides for good identification of sharp edge defects on the sample 103, such as those that appear in the case of stacking defects. DF-based inspection, however, provides for quality detection of point defects. Through the combination and/or comparison of DF and DIC signals, the controller 116 may more readily and more accurately detect and characterize a given set of defects. For example, the controller 116 may compare the DF signal and the DIC signal obtained from the same region of the sample 103 in order to correlate the DF-based features with the DIC-based features, allowing the controller 116 (or user) to more accurately characterize the one or more defects appearing in the given region.

In another embodiment, the controller 116 may independently analyze the DF signal from the DF sensor 112 and the DIC signal from the DIC sensor 114. In this regard, while the system 100 integrates the optical architecture of the DF signal and DIC signal detection, the controller 116 acts to analyze the DF and DIC signals independently from one another.

While much of the present disclosure has discussed the separation of the DF and DIC signals via a mirrored pupil mask 134, it is noted herein that such a configuration is not a limitation on the present disclosure and is provided merely for illustrative purposes. It is noted that any optical architecture suitable to separate the DF and DIC signals may be implemented in the context of the present disclosure.

FIG. 1D illustrates a simplified schematic of system 100, in accordance with an alternative embodiment of the present disclosure. It is noted herein that the various components and embodiments described in the context of FIGS. 1A-1C should be interpreted to extend to FIG. 1D unless otherwise noted.

The optical sub-system 104 depicted in FIG. 1D includes a pair of pupil structures 158, 159 arranged to separate the DF signal and the DIC signal collected from the sample 103. In one embodiment, the optical sub-system 104 includes a beam splitter 154 configured to reflect a first portion of the collected illumination along a DF path 111, while transmitting a second portion of the collected illumination along the DIC path 113. It is noted that this arrangement is not limiting and should be interpreted merely as an illustration. For instance, the beam splitter 154 may be arranged to reflect a portion of the collected illumination along the DIC path 113, while transmitting a portion of the collected illumination along the DF path 111.

In one embodiment, the first pupil structure 158 includes a pupil block, which serves to block illumination propagated along the DF path 111 having an NA below a selected NA threshold. Further, the second pupil structure 159 may include a pupil mask, which serves to block illumination propagated along the DIC path 113 having an NA above the selected NA threshold. In this regard, the pupil block 158 and pupil mask 159 are at conjugate to one another, whereby one structure transmits light in an NA regime that is blocked by the other structure. It is noted herein that the above pupil block 158/pupil mask arrangement 159 is not limiting and is provided merely for illustrative purposes. For example, the DF path 111 may include a pupil mask, with the DIC path 113 including a pupil block. In this regard, the pupil mask of the DF path 111 serves to block illumination propagated along the DF path 111 having an NA above a selected NA threshold, with the pupil block of the DIC path blocking illumination propagated along the DIC path 113 having an NA below the selected NA threshold. In another embodiment, the optical sub-system 104 may carry out the separation of the DF and DIC signals using only a pupil block 158, with no corresponding pupil structure in the DIC path 113 to limit the upper NA range.

In addition to the pupil mask 134, the optical sub-system 104 of FIG. 1D may include any number and type of optical components for directing, conditioning, and/or selecting illumination from the illumination source 102 and/or scattered or reflected illumination collected from the sample 103.

The illumination of interest may be processed by various optical elements such as, but not limited to, one or more polarizers, one or more wave plates, one or more beam shape components, one or more filters, and one or more folding mirrors prior to entering the objective 108 and illuminating the sample 103. For example, as shown in FIG. 1D, illumination from the illumination source 102 may be transmitted through the OD 120 (e.g., 3 position) and through a polarizer 122 and wave plate 124 (e.g., quarter wave plate). Then, the beam splitter 126 may direct some of the illumination from the illumination source 102 along an illumination path and through the objective 108 to the sample 103.

In another embodiment, the objective 108 collects the illumination scattered from the sample 103 to form the DF signal. The DF signal is then reflected by mirror 132 and directed back along the optical path through the filter 130 and afocal lens 128. Then, the collected illumination again impinges on the beam splitter 154, which serves to separate the collected signal into a first portion directed along the DF path 111 and a second portion directed along the DIC path 113. As noted previously herein, the pupil structures 158, 159 serve to block (or transmit) illumination above and below a selected NA threshold respectively. In the case of the DF path 111, after low NA light is blocked by the pupil block 158, the remaining high NA light is focused onto the DF sensor 112 (e.g., 1-D sensor suitable for large particle monitoring) via lens 142 (e.g., tube lens). In the case of the DIC path 113, after high NA light is blocked by the pupil mask 159, the remaining low NA light is focused onto the DIC sensor 114 (e.g., 2-D sensor) via lens 142 (e.g., tube lens).

The present disclosure is not limited to the specific configuration and architecture depicted in FIGS. 1A-1D and it is recognized herein that there are a number of ways in which a DF signal may be separated from a DIC signal.

In some embodiments, the inspection system described herein may be configured as a "stand alone tool" or a tool that is not physically coupled to a process tool. In other embodiments, such an inspection system may be coupled to a process tool (not shown) by a transmission medium, which may include wired and/or wireless portions. The process tool may include any process tool known in the art such as a lithography tool, an etch tool, a deposition tool, a polishing tool, a plating tool, a cleaning tool, or an ion implantation tool. The results of inspection performed by the systems described herein may be used to alter a parameter of a process or a process tool using a feedback control technique, a feedforward control technique, and/or an in situ control technique. The parameter of the process or the process tool may be altered manually or automatically.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. An apparatus for simultaneous dark field and differential interference contrast inspection comprising:
    one or more illumination sources;
    a sample stage configured to secure a sample;
    a first sensor;
    a second sensor; and
    an optical sub-system comprising:
        an objective;
        one or more optical elements arranged to direct, through the objective, illumination from the one or more illumination sources to a surface of the sample, wherein the objective is configured to collect a collected signal from the surface of the sample, wherein the collected signal includes at least one of a scattering-based signal and a phase-based signal from the sample; and
        one or more separation optical elements arranged to spatially separate the collected signal into a dark field signal and a differential interference contrast signal by directing the dark field signal along a dark field path to the first sensor and the differential interference contrast signal along a differential interference contrast path to the second sensor, wherein the one or more separation optical elements include a reflective pupil mask arranged to spatially separate the collected signal into a dark field signal and a differential interference contrast signal based on a selected NA threshold.

2. The apparatus of claim 1, further comprising:
a controller communicatively coupled to the first sensor and the second sensor, wherein the controller is configured to:
receive one or more measurements of the dark field signal associated with the sample from the first sensor; and
receive one or more measurements of the differential interference contrast signal associated with the sample from the second sensor.

3. The apparatus of claim 2, wherein the controller is further configured to perform a data fusion process to characterize one or more portions of the sample, simultaneously, with the received dark field signal and the received differential interference contrast signal.

4. The apparatus of claim 2, wherein the controller is further configured to perform a data fusion process to characterize one or more portions of the sample, independently, with at least one of the received dark field signal or the received differential interference contrast signal.

5. The apparatus of claim 1, wherein the reflective pupil mask of the optical sub-system comprises:
a mirrored pupil mask configured to reflect illumination having an NA larger than a selected NA threshold along a dark field path, the mirrored pupil mask further configured to transmit illumination having an NA smaller than the selected NA threshold along a differential interference contrast path.

6. The apparatus of claim 1, wherein the reflective pupil mask of the optical sub-system comprises:
at least a mirrored pupil mask configured to reflect illumination having an NA smaller than a selected NA threshold along a dark field path, the mirrored pupil mask further configured to transmit illumination having an NA larger than the selected NA threshold along a differential interference contrast path.

7. The apparatus of claim 1, wherein the one or more separation optical elements of the optical sub-system comprise:
a beam splitter configured to separate the collected signal into a first portion directed along the dark field path to the first sensor and a second portion directed along the differential interference contrast path to the second sensor.

8. The apparatus of claim 1, wherein the one or more illumination sources comprise:
one or more lasers.

9. The apparatus of claim 1, wherein the first sensor comprises:
a one-dimensional sensor.

10. The apparatus of claim 1, wherein the second sensor comprises:
a two-dimensional sensor.

11. The apparatus of claim 1, wherein the apparatus is configured as a wafer inspection tool.

12. The apparatus of claim 1, wherein the apparatus is configured as a microscope for a biological sample.

13. An apparatus for simultaneous dark field and differential interference contrast inspection comprising:
one or more illumination sources;
a sample stage configured to secure a sample; and
an optical sub-system comprising:
an objective;
a mirrored pupil mask configured to transmit illumination having an NA below a selected NA threshold;
one or more optical elements arranged to direct illumination having an NA below the selected NA threshold through the mirrored pupil mask, wherein the one or more optical elements are further configured to direct illumination transmitted through the mirrored pupil mask through the objective and to a surface of the sample,
wherein the objective is configured to collect a collected signal from the surface of the sample, wherein the collected signal includes at least one of a scattering signal and a phase signal from the sample,
wherein the mirrored pupil mask is further configured to spatially separate the collected signal into a dark field signal and a differential interference contrast signal by reflecting a portion of the collected illumination having an NA above the selected NA threshold along a dark field path to a first sensor and transmitting a portion of the collected illumination having an NA below the selected NA threshold along the differential interference contrast path to a second sensor.

14. The apparatus of claim 13, wherein the one or more illumination sources comprise:
one or more lasers.

15. The apparatus of claim 13, wherein the first sensor comprises:
a one-dimensional sensor.

16. The apparatus of claim 13, wherein the second sensor comprises:
a two-dimensional sensor.

17. The apparatus of claim 13, wherein the apparatus is configured as a wafer inspection tool.

18. The apparatus of claim 13, wherein the apparatus is configured as a microscope for a biological sample.

19. An apparatus for simultaneous dark field and differential interference contrast inspection comprising:
one or more illumination sources;
a sample stage configured to secure a sample; and
an optical sub-system comprising:
an objective;
one or more optical elements configured to direct illumination through the objective and to a surface of the sample, wherein the objective is configured to collect a collected signal from the surface of the sample, wherein the collected signal includes at least one of a scattering signal and a phase signal from the sample,
a beam splitter configured to direct a first portion of the collected illumination along a dark field path, wherein the beam splitter is further configured to transmit a second portion of the collected illumination along the differential interference contrast path;
a pupil block disposed along the dark field path and configured to block illumination having an NA below a selected NA threshold; and
a pupil mask disposed along the differential contrast interference path and configured to block illumination having an NA above the selected NA threshold;
a first sensor configured to collect illumination transmitted by the pupil block of the dark field path; and
a second sensor configured to collect illumination transmitted by the pupil mask of the differential interference contrast path.

20. The apparatus of claim 19, wherein the one or more illumination sources comprise:
one or more lasers.

21. The apparatus of claim 19, wherein the first sensor comprises:
a one-dimensional sensor.

22. The apparatus of claim 19, wherein the second sensor comprises:
a two-dimensional sensor.

23. The apparatus of claim 19, wherein the apparatus is configured as a wafer inspection tool.

24. The apparatus of claim 19, wherein the apparatus is configured as a microscope for a biological sample.

* * * * *